US00PP14710P2

(12) United States Plant Patent
Oudshoorn

(10) Patent No.: US PP14,710 P2
(45) Date of Patent: Apr. 20, 2004

(54) CAMPANULA PLANT NAMED 'LA BELLO'

(50) Latin Name: *Campanula persicifolia*
Varietal Denomination: La Bello

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 10/421,318

(22) Filed: Apr. 23, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Campanula plant named 'La Bello', characterized by its upright growth habit; double white-colored campanulate flowers; and temperature tolerance from −30 to 40° C.

2 Drawing Sheets

Botanical classification/cultivar designation: *Campanula persicifolia* cultivar La Bello.

BACKGROUND OF THE INVENTION

The present Invention relates to a new and distinct cultivar of Campanula plant, botanically known as *Campanula persicifolia*, and hereinafter referred to by the name 'La Bello'.

The new Campanula originated from a cross-pollination made by the Inventor in 2000 of two unidentified selections of *Campanula persicifolia*, not patented.

Asexual reproduction of the new cultivar by cuttings taken at Rijpwetering, The Netherlands since 2000, has shown that the unique features of this new Campanula are stable and reproduced true to type in successive generations.

SUMMARY OF THE INVENTION

Plants of the cultivar La Bello have not been observed under all possible environmental conditions. The phenotype may vary somewhat with variations in environment such as temperature and/or light intensity without, however, any variance in genotype.

The following traits have been repeatedly observed and are determined to be the unique characteristics of 'La Bello'. These characteristics in combination distinguish 'La Bello' as a new and distinct cultivar:

1. Upright growth habit.
2. Double white-colored campanulate flowers.
3. Temperature tolerance from −30 to 40° C.

Plants of the new Campanula differ from plants of the parent selections and cultivars known to the Inventor in flower color and flower form.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ from the color values cited in the detailed botanical description which accurately describe the colors of the new Campanula.

The photograph on the first sheet comprises a side perspective view of a typical plant of 'La Bello'.

The photograph at the top of the second sheet is a close-up view of typical flowering stems of 'La Bello'.

The photograph at the bottom of the second sheet is a close-up view of typical leaves of 'La Bello'.

DETAILED BOTANICAL DESCRIPTION

In the following description, color references are made to The Royal Horticultural Society Colour Chart, 2001 Edition, except where general terms of ordinary dictionary significance are used. Plants used for the above-mentioned photographs and botanical description were grown in Lisserbroek, The Netherlands in an outdoor nursery in containers during the summer. During the production of the plants, day temperatures ranged from 14 to 27° C. and night temperatures ranged from 4 to 16° C. Plants used for the photographs and description were about two years old.

Botanical classification: *Campanula persicifolia* cultivar La Bello.

Parentage:

*Female, or seed, parent.*—Unidentified selection of *Campanula persicifolia*, not patented.

*Male, or pollen, parent.*—unidentified selection of *Campanula persicifolia*, not patented.

Propagation:

*Type.*—By cuttings.

*Time to initiate roots.*—About 90 days at 18° C.

*Root description.*—Fibrous, fine; light brown to white in color.

Plant description:

*Form.*—Upright plant habit; vigorous growth habit.

*Plant height, soil level to top of plant plane.*—About 80 cm.

*Plant width.*—About 28 cm.

*Lateral branch description.*—Quantity: About seven per plant. Length: About 24 cm. Diameter: About 2 to 6 mm. Internode length: About 4.4 cm. Texture: Smooth, glabrous. Color: 143A.

*Foliage description.*—Arrangement: Alternate, simple. Length: About 12.6 cm. Width: About 1.6 mm. Shape: Linear to narrowly oblanceolate. Apex:

Acute. Base: Cuneate; decurrent. Margin: Serrate. Texture, upper and lower surfaces: Smooth, glabrous. Venation pattern: Pinnate. Color: Developing foliage, upper surface: 143A. Developing foliage, lower surface: 143B. Fully expanded foliage, upper surface: 137A. Fully expanded foliage, lower surface: 137C. Venation, upper and lower surfaces: 144C.

Flower description:

*Flower type and habit*.—Double campanulate flowers arranged in terminal racemes. Flowers face mostly outwardly to drooping. Flowers not persistent.

*Fragrance*.—None.

*Natural flowering season*.—Continuously flowering from mid-June to Mid-August.

*Quantity*.—Freely flowering with about 33 flowers and flower buds per lateral branch.

*Flower longevity on the plant*.—About seven days.

*Inflorescence length*.—About 20 cm.

*Inflorescence diameter*.—About 11 cm.

*Flower diameter*.—About 4.5 cm.

*Flower depth* (*height*).—About 2.5 cm.

*Flower buds*.—Length: About 1.8 cm. Diameter: About 1.6 mm. Shape: Oblong. Color: 145D to 157A.

*Petals*.—Quantity per flower: About five. Length: About 2.7 cm. Width: About 2.1 cm. Shape: Broadly ovate. Apex: Acute. Margin: Entire. Texture, upper and lower surfaces: Smooth; glabrous. Color: When opening and fully opened, upper surface: 91B fading to close to 155D towards the base; apex, 144C to 144D; color becoming closer to 155D with apex, 145D. When opening and fully opened, lower surface: 91C fading to close to 155D towards the base; apex, 144C to 144D.

*Petaloids*.—Quantity per flower: About 20 in about five whorls. Length: About 2.6 cm. Width: About 2 cm. Shape: Broadly obovate. Apex: Acute. Margin: Entire. Texture, upper and lower surfaces: Smooth; glabrous. When opening and fully opened, upper surface: Close to 155D; towards the apex, 91C. When opening and fully opened, lower surface: Close to 155D; towards the apex, 91D.

*Sepals*.—Quantity per flower: About five. Length: About 1.5 cm. Diameter: About 5 mm. Shape: Lanceolate. Apex: Acuminate. Base: Cuneate. Margin: Entire. Color, upper and lower surfaces: 137A.

*Peduncles*.—Length: About 20 cm. Diameter: About 3 mm. Strength: Strong. Color: 143A.

*Pedicels*.—Length: About 4.7 cm. Diameter: About 2 mm. Strength: Strong. Color: 143A to 143B.

*Reproductive organs*.—Androecium: Stamens per flower: About ten. Anther shape: Narrowly oblong. Anther length: About 6 mm. Anther color: 161B to 162C. Pollen amount: Moderate. Pollen color: 11C to 11D. Gynoecium: Quantity of pistils per flower: One. Pistil length: About 1.7 cm. Stigma shape: Terete. Stigma color: 150D. Style length: About 4 mm. Style color: 150D. Ovary color: 137A. Seeds/fruits: Seed and fruit development has not been observed.

Disease/pest resistance: Under commercial production conditions, plants of the new Campanula have not been noted to be resistant to pathogens or pests common to Campanula.

Temperature tolerance: Pllants of the new Campanula have been observed to tolerate temperatures from −30 to 40° C. in Rijpwetering, The Netherlands.

It is claimed:

1. A new and distinct cultivar of Campanula plant named 'La Bello', as illustrated and described.

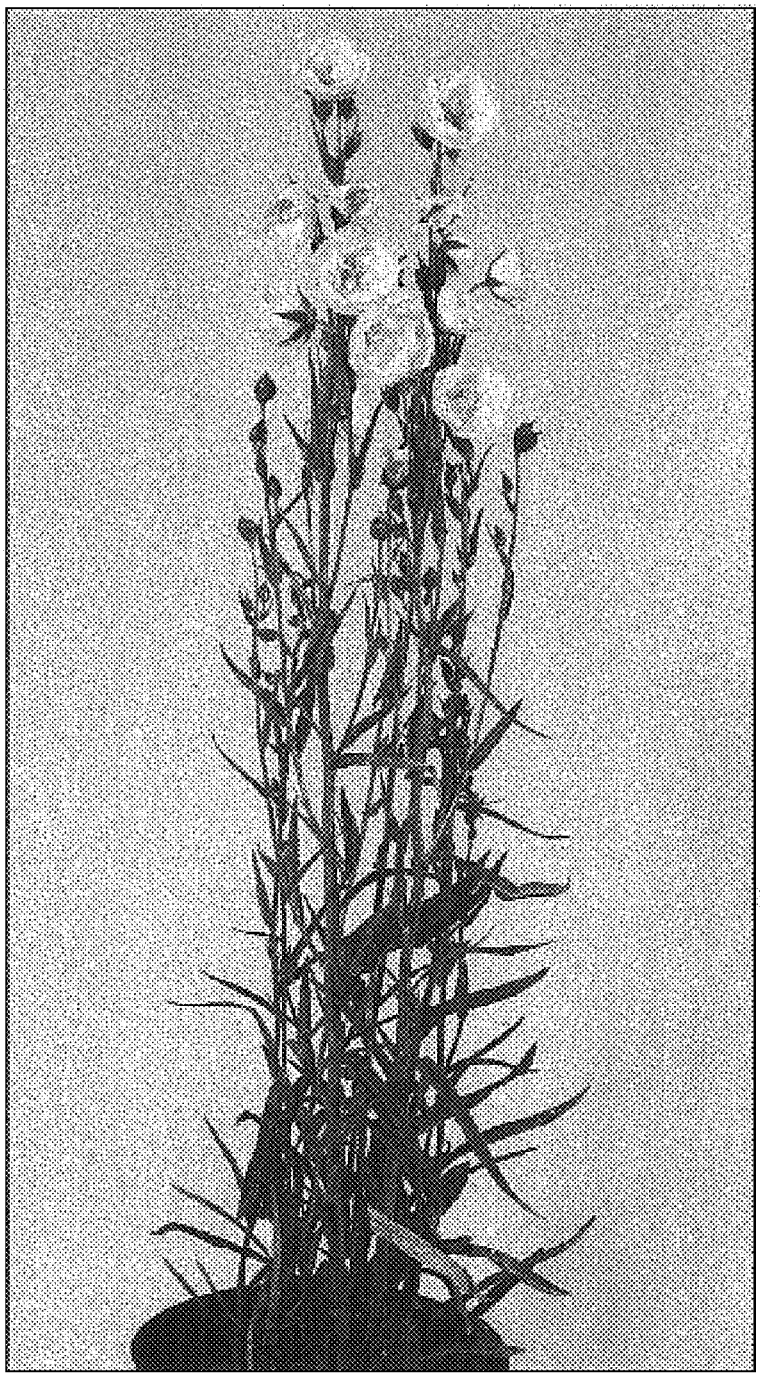

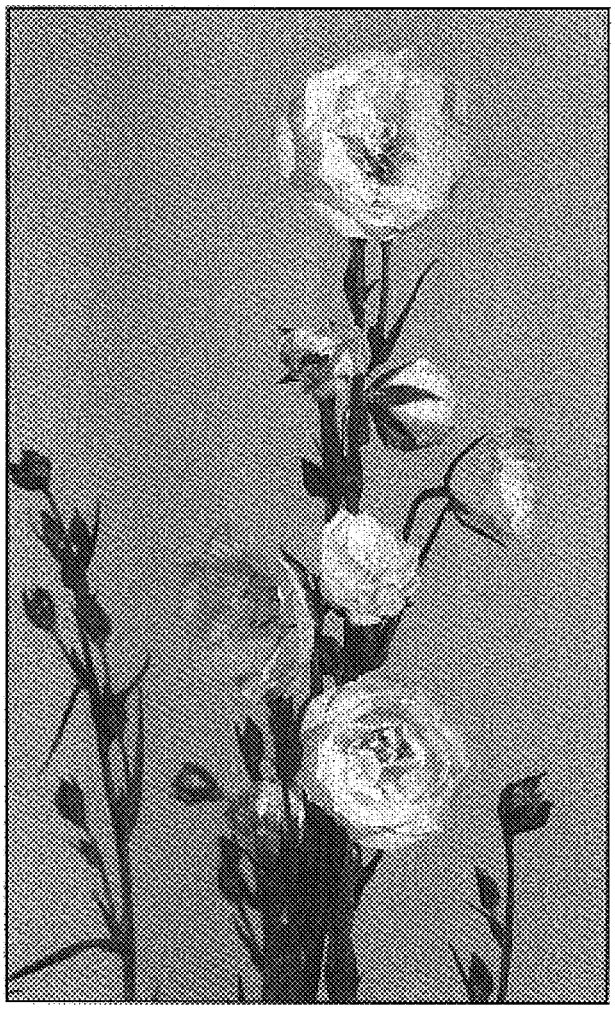
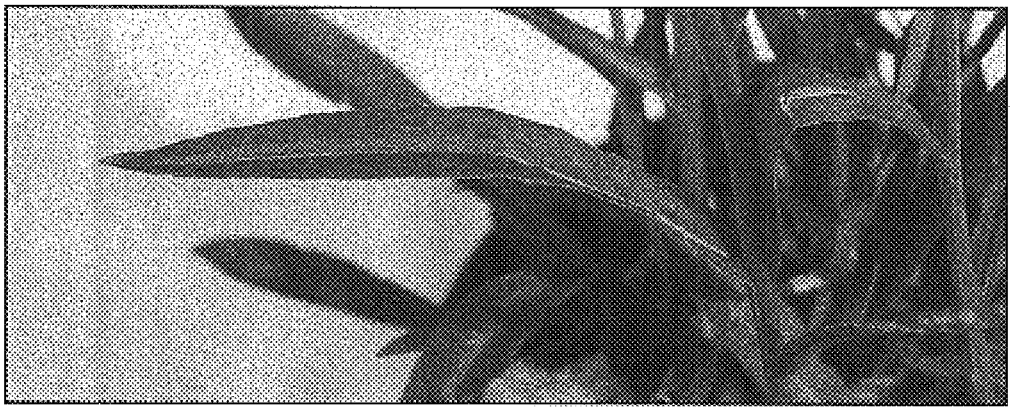

* * * * *